US010012615B1

(12) United States Patent
Mergelas

(10) Patent No.: US 10,012,615 B1
(45) Date of Patent: Jul. 3, 2018

(54) IMPEDANCE PROBE FOR DETECTING BREAKS IN PRESTRESSED CONCRETE PIPE

(71) Applicant: 1440814 Ontario Inc., Etobicoke (CA)

(72) Inventor: Brian Mergelas, Etobicoke (CA)

(73) Assignee: 1440814 ONTARIO INC., Etobicoke (CA)

( * ) Notice: Subject to any disclaimer, the term of this patent is extended or adjusted under 35 U.S.C. 154(b) by 0 days.

(21) Appl. No.: 15/657,653

(22) Filed: Jul. 24, 2017

(51) Int. Cl.
*G01N 27/90* (2006.01)
*G01N 27/02* (2006.01)

(52) U.S. Cl.
CPC ......... *G01N 27/902* (2013.01); *G01N 27/023* (2013.01)

(58) Field of Classification Search
USPC ........................................ 324/318, 220, 221
See application file for complete search history.

(56) References Cited

U.S. PATENT DOCUMENTS

| | | | | |
|---|---|---|---|---|
| 3,444,459 A * | 5/1969 | Feinman | ............ | G01N 27/9033 324/242 |
| 5,126,654 A * | 6/1992 | Murphy | ................. | G01N 17/02 204/196.06 |
| 6,127,823 A | 10/2000 | Atherton | | |
| 6,781,369 B2 | 8/2004 | Paulson et al. | | |
| 6,791,318 B2 | 9/2004 | Paulson et al. | | |
| 7,002,340 B2 | 2/2006 | Atherton | | |
| 2003/0164698 A1* | 9/2003 | Paulson | ................. | G01N 27/82 324/220 |
| 2004/0189289 A1* | 9/2004 | Atherton | .............. | G01N 27/902 324/220 |
| 2009/0231151 A1* | 9/2009 | Korolev | ................. | G01N 27/20 340/657 |
| 2013/0009632 A1* | 1/2013 | Yamamoto | ......... | G01N 27/9046 324/222 |
| 2013/0214771 A1* | 8/2013 | Tiernan | ................ | G01N 27/904 324/242 |
| 2015/0097589 A1* | 4/2015 | Orazem | ................. | G01N 27/02 324/693 |

OTHER PUBLICATIONS

L.S. Obtrusky et al., "Transmit-Receive Eddy Current Probes"; AECL Research, Nondestructive Testing Development Branch, Chalk River Laboratories, Chalk River, Ontario K0J 1J0.
Javier Garcia-Martin et al., "Non-Destructive Techniques Based on Eddy Current Testing"; Sensors, 2011:11:2525-2565.

* cited by examiner

*Primary Examiner* — Patrick Assouad
*Assistant Examiner* — Demetrius Pretlow
(74) *Attorney, Agent, or Firm* — Thomas Horstemeyer, LLP

(57) ABSTRACT

A method is provided for inspecting a prestressed concrete pipe (PCP). An impedance probe is passed along the PCP. As the impedance probe travels along the PCP, a magnetic field within the impedance probe is generated and the impedance of the impedance probe is measured. The measured impedances are analyzed for anomalies, which may indicate broken prestressed wires. RFT probes, which are what are typically used for inspecting PCPs, require axial separation of two coils, one being an exciter coil and the other being a passive detector coil. However, there is only a single coil in an impedance probe and so the apparatus used to inspect the PCP is not as large axially. The apparatus used to inspect the PCP is simpler to set up than if an RFT probe is used, and coupling between a transmitter and a receiver is not a concern.

12 Claims, 5 Drawing Sheets

IMPEDANCE PROBE FOR DETECTING BREAKS IN PRESTRESSED CONCRETE PIPE

FIELD OF THE INVENTION

The invention relates to non-destructive testing of prestressed concrete pipe, and more particularly to use of distortions of magnetic fields to detect breaks in such pipes.

BACKGROUND OF THE INVENTION

Prestressed concrete pipe (PCP) consists of a concrete pipe that is prestressed using high strength prestressing metal wires wound around the concrete pipe to approximately 70% of yield strength. The concrete pipe may or may not also have longitudinal pre-stressing strands, and may or may not also have a steel cylinder embedded within or lined with concrete. A PCP is designed to operate under pressure in such a way that the concrete core remains under compression for all operating conditions of the pipeline. The design of individual sections of the PCP along the length of a pipeline may vary as the operating pressures change.

Breaks in the pre-stressing wires, such as caused by corrosion or hydrogen embrittlement, result in a localized loss of prestress in the concrete core, which can lead to a sudden rupture of a pressurized pipeline. It is therefore beneficial to be able detect broken prestressing wires in a given section of pipe, such as through periodic inspections of the pipeline In addition, pipeline contractors have been known to install sections of pipe in an incorrect order, resulting in a weaker pipe experiencing high pressures which exceed its design. It is therefore also beneficial to be able to know if the right pipe section has been laid in the right location.

One method of non-destructive testing of pipe is called Remote Field Testing (RFT). A RFT probe consists of an exciter coil which sends a signal to a detector coil, although there may be more than one detector coil, may be more than one exciter coil, or exciters and/or detectors other than coils may be used. The exciter coil is energized with an AC current and emits a magnetic field. In the case of pipe in which a metal cylinder is embedded in concrete, the magnetic field travels outwards from the exciter coil, through the pipe wall, and along the pipe. The detector coil is placed inside the pipe two to three pipe diameters away from the exciter coil and detects the magnetic field that has traveled back in from the outside of the pipe wall (for a total of two through-wall transits). In areas of metal loss, the field arrives at the detector with a faster travel time (less phase lag) and greater signal strength (amplitude) due to the reduced path through the steel.

In PCPs, the prestressed wires are located away from the inner surface of the pipe, and an RFT probe can be used to detect breaks in prestressed wires. U.S. Pat. No. 6,127,823, issued Oct. 3, 2000, discloses such a method in which the pipe is a PCP. In PCPs, there is a transformer coupling (TC) effect, in which the magnetic field produced by the exciter coil induces a current in the prestressing wires wound around the pipe, which in turn induces a current in the detector coil. In a PCP in which a metal cylinder is embedded in the concrete wall of the pipe, the signal detected by the detector coil is therefore a combination of a signal induced by the TC effect and a signal propagated along the outside of the pipe. Using anomalies in this detected signal, abnormalities such as prestressing wire breaks can be detected.

The receiver coil is spaced far enough away longitudinally from the exciter coil that direct field effects are negligible. Magnetic shielding may also be used between the exciter coil and the detector coil to further reduce direct field effects. The wide spacing is necessary so that the detector coil is within the remote field zone of the exciter coil in order that the detector coil only (or at least predominantly) detects fields that are transmitted through the pipe and that interact with the prestressing wires. The use of two coils may require more time to set up the apparatus. An operator must also ensure that there is no coupling between the transmitter and the receiver, or at least that such coupling is minimized. The detected signal may also include spurious signals resulting from movement of the coils relative to each other or relative to the pipe axis.

Impedance probes offer another way of performing non-destructive testing of pipe in order to detect flaws. This is often referred to as Eddy-current Testing (ECT). In ECT a small circular coil, typically much less than one to two inches in diameter and much less than three inches long, carrying current is placed in proximity to the pipe, which must be electrically conductive. The alternating current in the coil or coils generates a changing magnetic field which interacts with the conducting pipe and induces eddy currents within the metal cylinder embedded in the pipe wall. Variations in the phase and magnitude of these eddy currents can be monitored using a second receiver coil, or by measuring changes to the current flowing in the primary excitation coil if a single coil is being used. Variations in the electrical conductivity or magnetic permeability of the pipe, or the presence of any flaws, will cause a change in eddy current and a corresponding change in the phase and amplitude of the measured current. ECT can detect very small cracks in or near the surface of the pipe, such as corrosion pitting or cracking.

ECT does have several limitations, however. Only conductive materials can be tested. In general, the surface of the material must be accessible, and the depth of penetration into the material is limited by the conductivity and permeability of the metal lining, as well as the operating frequency of the ECT probe. This makes conventional ECT probes impractical for detecting breaks in prestressing wire located on the far side of metallic cylinders. Even if no metal cylinder is present, several inches of concrete between the ECT probe and the prestressing wires will create a large lift off between the probe and the wires. This greatly reduces the capability of conventional ECT probes in analyzing prestressing wires. For these reasons, impedance probes are not used for inspecting for breaks in prestressing wires in PCPs.

SUMMARY OF THE INVENTION

In accordance with one aspect of the invention, a method is provided for inspecting a prestressed concrete pipe (PCP). An impedance probe is passed along the PCP. At each of a multitude of locations along the PCP, a magnetic field is generated by driving a time-varying current through the impedance probe, and the impedance of the impedance probe is measured. The measured impedance at each of the locations is then analyzed. It may be concluded from any unexpected anomaly in the measured impedance that a break in prestressed wire of the PCP is likely at the location associated with the measured impedance containing the unexpected anomaly.

In one embodiment, the impedance coil comprises a single coil. In other embodiment the impedance coil comprises multiple coils. In such an embodiment, a magnetic field is generated by driving the time-varying current through each of the coils, the impedance of each of the coils is measured, and the measured impedances of all of the coils is analyzed. In yet another embodiment, multiple impedance probes are used. In such an embodiment, a magnetic field is generated by driving a respective time-varying current through each of the impedance probes, the impedance of each of the impedance probes is measured, and the measured impedances of all of the impedance probes is analyzed.

By examining for breaks in prestressed wire using an impedance probe, the complications associated with separate transmit and receive coils can be avoided. By using a large impedance probe, magnetic fields produced by the probe are strong enough to induce currents in the prestressing wires despite large lift off, and the induced currents are powerful enough to change the impedance of the impedance probe through back-induction.

BRIEF DESCRIPTION OF THE DRAWINGS

The features and advantages of the invention will become more apparent from the following detailed description of the preferred embodiment(s) with reference to the attached figures, wherein.

It will be noted that in the attached figures, like features bear similar labels.

DETAILED DESCRIPTION OF THE EMBODIMENTS

Figure 1:
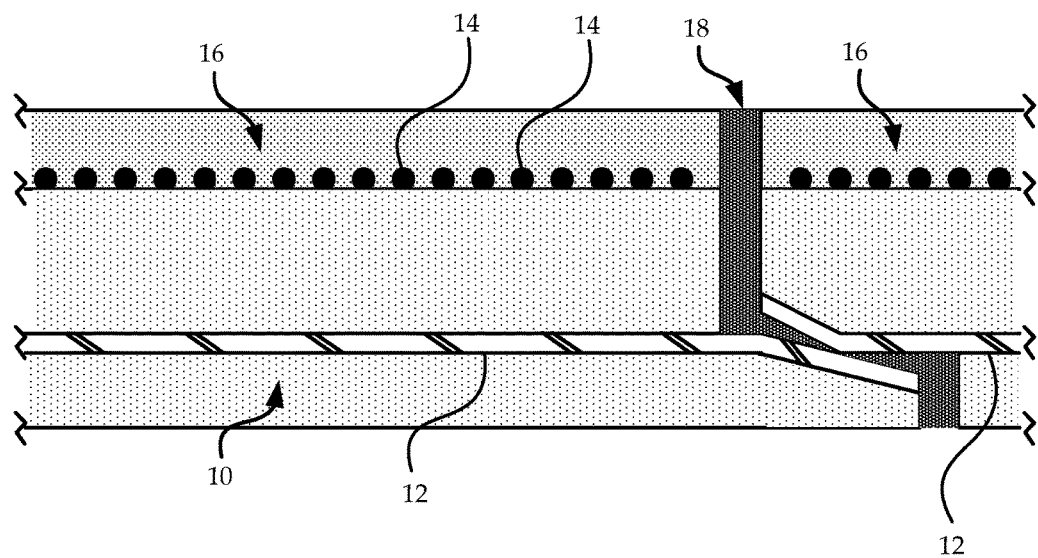
FIG. 1 is a diagram of a portion of an example prestressed concrete pipe (PCP) wall.

Referring to FIG. 1, a cross-section of a portion of an example prestressed concrete pipe (PCP) wall is shown. The central axis of the pipe is shown as a dot-dashed line, although the distance of this line from the wall of the pipe is not to scale with the illustrated structure of the wall. The PCP is composed mostly of concrete 10. A metal cylinder 12 is embedded in the concrete. Surrounding the concrete is a continuous coil of metal wire 14. Only some of the turns of the prestressed wire 14 are labeled as such in FIG. 1 for clarity, but the same symbol is used throughout FIG. 1 to illustrate the windings. Overlaying and embedding the metal wire 14 is a coating of impacted mortar 16.

The PCP is composed of sections, which are placed sequentially and joined together when the PCP is installed. FIG. 1 shows the abutting ends of two sections of the pipe. The sections are joined using a cement mortar 18. The location of the joining of two sections is more complicated than that shown in FIG. 1. For example, FIG. 1 shows the metal cylinder 12 of each section overlapping. In reality, there is typically a rubber gasket, a spigot ring, and a bell ring, none of which are shown in FIG. 1. However, for the purposes of describing the invention, it must only be understood that there is a discontinuity of materials at the joining of two sections of the PCP. Also not shown in FIG. 1 are anchors fastening the prestressing wire 14 to the impacted mortar 16 and shorting straps that run under longitudinally under the prestressing wire 14.

The portion of PCP shown in FIG. 1 is an example only. More generally, there may or may not be a metal cylinder 12 embedded within or lined with the concrete 10.

Figure 2:
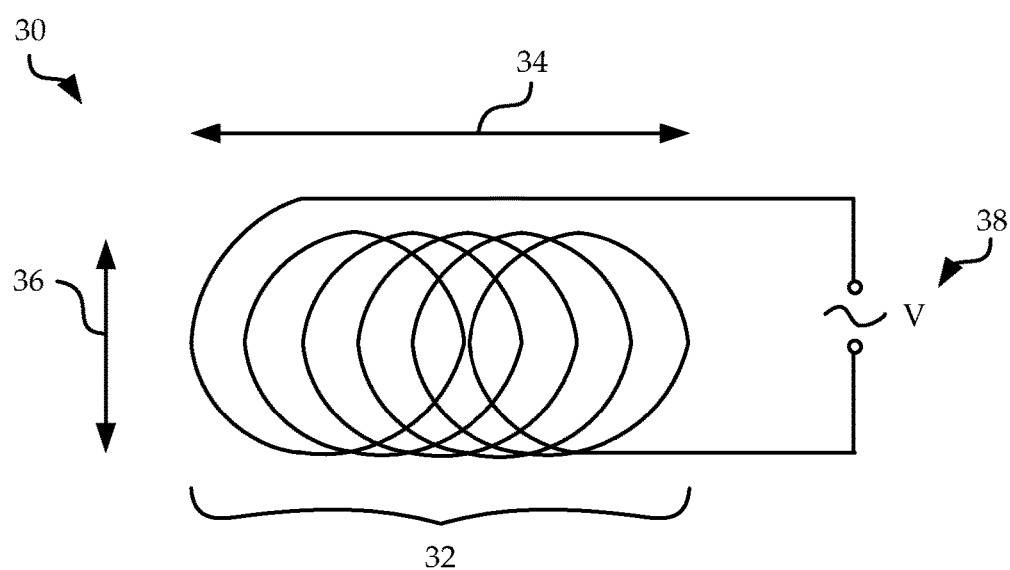
FIG. 2 is a schematic diagram of an impedance probe according to one embodiment of the invention.

Referring to FIG. 2, a schematic diagram of an impedance probe 30 according to one embodiment of the invention is shown. The impedance probe 30 comprises a single solenoid 32 having a length 34 and a diameter 36. The solenoid is much larger than that in conventional impedance probes. Example dimensions of the solenoid 32 are a length 34 of three feet and a diameter 36 of fifteen inches. The solenoid 12 typically has thousands of turns of the conducting wire. However, it should be emphasized that these are only example dimensions. Other dimensions are possible as long as a magnetic field strong enough to generate induction currents in the prestressed wire is generated, although to be practical the dimensions of the impedance probe 30 should be small enough to fit through a maintenance hatch of a PCP so that it can operated within the PCP. The impedance probe 30 also has a time varying voltage source 38, which drives a time varying current through the solenoid 32 resulting in generating of a magnetic field.

Figure 3:
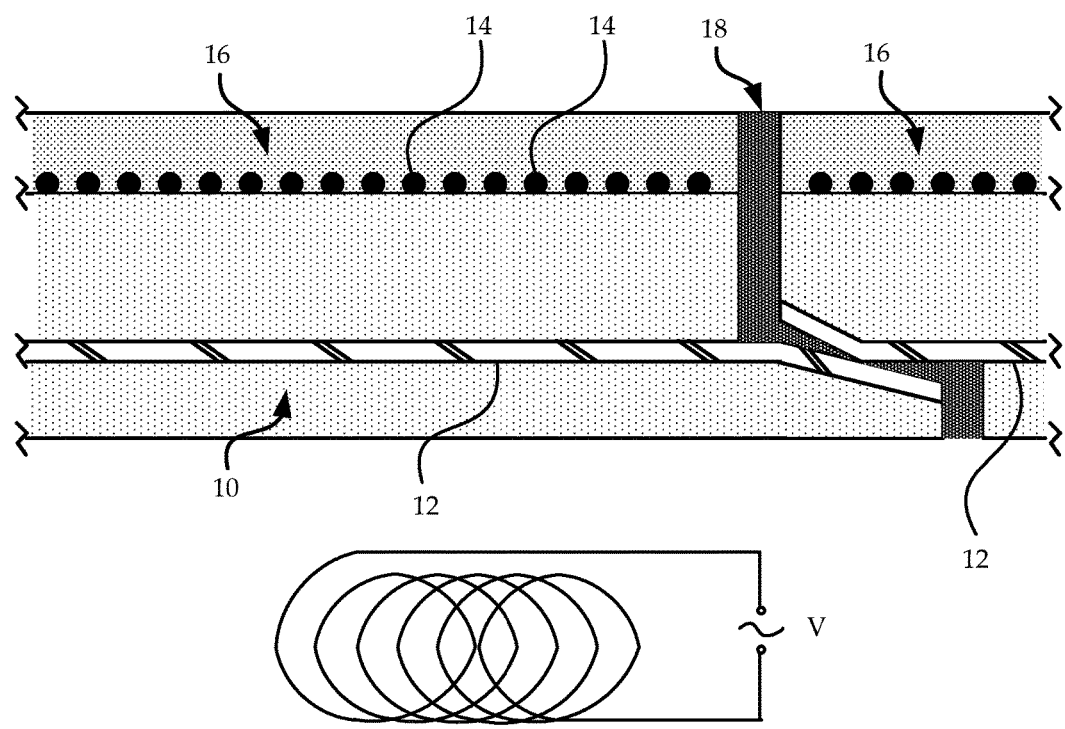
FIG. 3 is a diagram of the impedance probe of FIG. 2 within a PCP according to one embodiment of the invention.

Referring to FIG. 3, a diagram of the impedance probe 30 within a PCP according to one embodiment of the invention is shown. The prestressed wire 14 is spaced away from the interior surface of the PCP, such that the impedance probe 30 must be spaced apart from the prestressed wire 14. The impedance probe is oriented such that the axis of the solenoid 32 is parallel to the axis of the PCP.

The impedance of the impedance probe 30 is given by the equation $$Z=V/I$$

where V is the time-varying voltage driving current through the solenoid 32 and I is the measured current through the solenoid 32. The impedance Z has a real component and a complex component, with $$Z=R+iX$$

$$X=\omega L+1/\omega C$$

where R is the resistive component of the measured impedance, X is the reactive component of the measured impedance, L is the total inductance of the measured impedance, C is the total capacitance of the measured impedance, and $\omega$ is the frequency of the time-varying voltage driving current through the solenoid 32.

Figure 4:
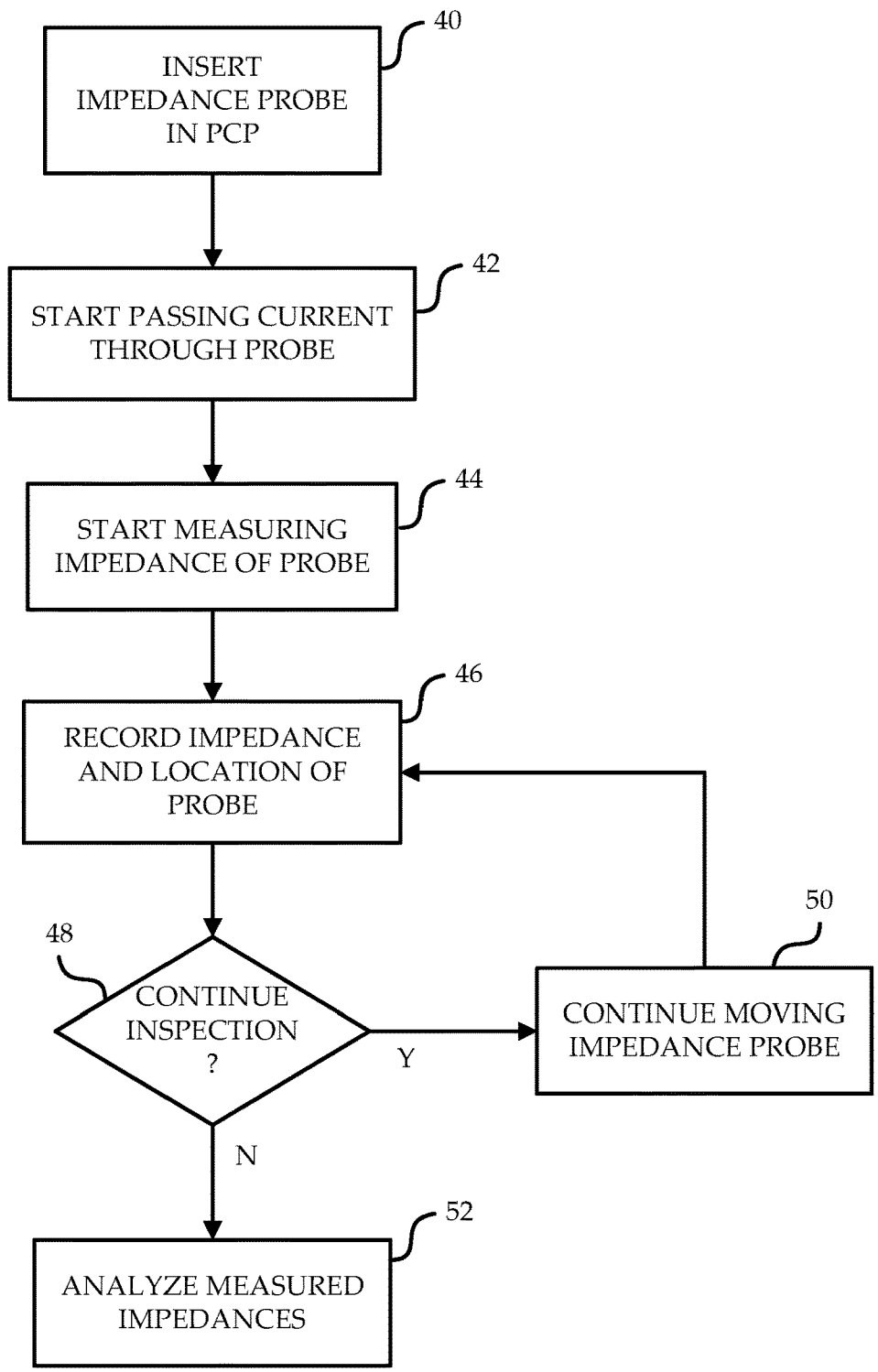
FIG. 4 is a flowchart of a method carried out using the impedance probe of FIG. 2 according to one embodiment of the invention.

Referring to FIG. 4, a flowchart of a method carried out using the impedance probe of FIG. 2 to inspect a PCP according to one embodiment of the invention is shown. At step 40 the impedance probe 30 is inserted within the PCP, such as through a maintenance hatch.

At step 42 a time-varying voltage is applied to the solenoid 32 of the impedance probe 30, driving a time-varying current through the solenoid 32. The time-varying current within the solenoid 32 causes the impedance probe 30 to generate a magnetic field. The strength of the magnetic field generated by a solenoid carrying a time-varying current is a function of both the strength of the current and the number of turns in the solenoid. Conventional impedance probes have such small dimensions that in order to obtain a magnetic field strong enough to induce current in the prestressed wires 14, small wire may have to be used so as to have a large number of turns. Smaller wire has higher resistance, however, and current must be kept low in order that the wire not burn out. A conventionally sized impedance probe cannot generate the strong magnetic fields necessary for inspection of PCP as described herein, and ECT is typically only used for tubes only a few inches in diameter. However, using a solenoid of larger dimensions than used in conventional impedance probes allows a larger number of turns without the need for narrow wire, and hence also allows a higher current to be used.

At step 44 measurement of the impedance of the impedance probe 30 is begun. Measurement of the impedance is carried out continuously during inspection of the PCP. The impedance is measured by measuring the voltage across the solenoid both in phase with the driving current and 90 degrees out of phase with the driving current, and comparing it with the driving current. Techniques of measuring and recording the time varying voltage in a detector coil in an RFT probe are known to those skilled in the art, and may also be used to measure and record the impedance in the single coil impedance probe of the invention. However, in an RFT probe the potential difference of the detector coil is compared with the driving current of the exciter coil. In the present invention a single coil is used, and the voltage measured across the coil is compared with the driving current applied to the same coil.

At step 46 the location of the impedance probe 30 and the measured impedance within the impedance probe 30 are recorded. The location of the impedance probe 30 may be determined in any manner. Examples of location determination include a GPS unit travelling with the impedance probe indicating location relative to a fixed point, or an odometer that measures distance traveled along the PCP since the insertion point. The location of the impedance probe 30 may be recorded on any device. Examples include a memory travelling with the impedance probe 30, a remote device in wireless communication with the impedance probe 30, and a remote device in communication with the impedance probe 30 via cables. The impedance of the impedance probe 30 is recorded in association with the recorded location of the probe, or with some other variable that allows such an association to be made later.

At step 48 it is determined whether to continue inspection of the PCP. If so, the impedance probe continues moving to a new location at step 50, and the location and measured impedance of the impedance probe recorded at a new location along the PCP. This continues until inspection of the PCP ends.

If it is determined at step 48 that inspection of the PCP is not to continue, then at step 52 the results are analyzed. This may be done at any time, and substantial time may elapse between ending of inspecting the PCP and analysis of the recorded impedances at step 52.

In operation, the impedance probe may inspect the pipeline over fifty or more sections before the recorded impedance is analyzed. A pipeline comprises many sections of PCP. Each section is connected to an adjoining section at a joint. As described above with reference to FIG. 1, when a metal cylinder is included in the PCP the metal cylinders of two sections overlaps at the joint, and the joint also includes a rubber gasket, a spigot ring, and a bell ring. Even if there is no metal cylinder, the joint still exhibits a discontinuity of materials, in the form of cement mortar and, more importantly, a discontinuity in the prestressed wire 14.

The measured impedance is a function of the inherent properties of the impedance probe 30 and also of surrounding conducting and ferromagnetic objects that can be electromagnetically coupled to the solenoid 32, including the prestressed wire 14. Since the prestressed wire 14 and any metal cylinder 12 are intended to be uniform, aside from joints between sections of the PCP and access hatches, the measured impedance will be regular with changes in position of the impedance probe 30, aside from when the impedance probe is next to joints or access hatches. The locations of joints and access hatches are known, and anomalies in the measured impedance at these locations are expected, and in the case of joints the anomalies may even be periodic.

There will also be small changes in measured impedance caused by anchors and shorting straps. Since the impedance probe inspects a large number of sections of pipeline and most of these sections will not contain breaks in the prestressed wire, the measured impedance for normal sections of pipeline can be known.

If there is a break in the prestressed wire 14, however, then the current induced in the impedance probe by this part of the prestressed wire 14 will change and a large anomaly in the measured impedance will appear. Any such large anomaly at a location away from an expected discontinuity, such as next to a joint or next to an access hatch, indicates a likelihood, or at least a possibility, of a break in the prestressed wire 14 at that location.

These anomalies are usually too small to be seen using conventional impedance probes if they are caused by breaks in the prestressed wire 14. This is because the magnetic field generated by conventional impedance probes is not powerful enough to induce significant eddy currents in the prestressed wire 14 because of the lift-off between the impedance probe and the prestressed wire 14. The lack of significant eddy currents in the prestressed wire 14 in turn means there is no significant induced current in the conventional impedance probe, and so the effects of breaks in the prestressed wire 14 are not usually seen when analyzing the measured impedances. For this reason, conventional impedance probes are not used to detect breaks in prestressed wires of PCPs. However, with large enough generated magnetic fields realized by large coils and/or large currents, significant eddy currents are induced in the prestressed wire 14 despite lift-off. These in turn induce a current in the impedance probe, and anomalies caused by breaks in the prestressed wire 14 can be seen as anomalies in the measured impedance of the impedance probe.

The invention has been described in which the analysis carried out at step 52 is performed subsequent to traversal of the impedance probe 30 through the PCP. Alternatively, analysis can be carried out in real-time as the impedance probe 30 traverses the PCP. In such an embodiment, an alarm may be generated when the real-time analysis of the measured impedance of the impedance probe 30 indicates a break in the prestressed wire 14 of the PCP, or if the real-time analysis of the measured impedance indicates greater than a threshold number of breaks.

Figure 5:
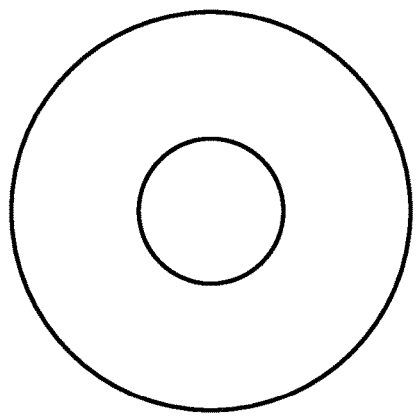
FIG. 5 shows various example configurations of impedance probe or probes within a PCP according to embodiments of the invention.
Figure 5:
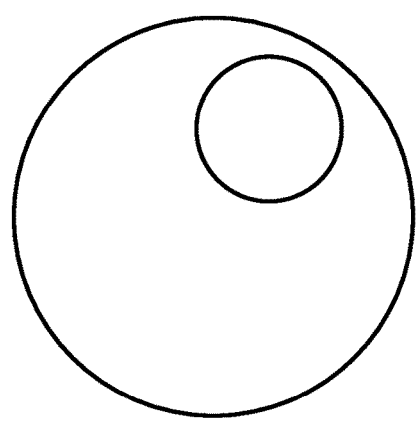
Figure 5:
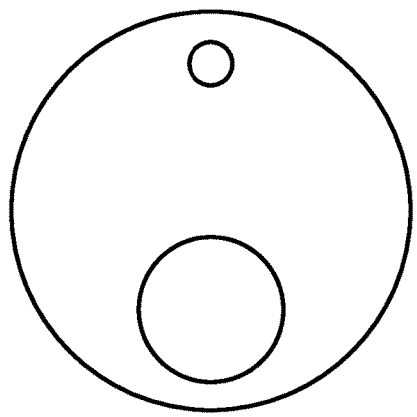
Figure 5:
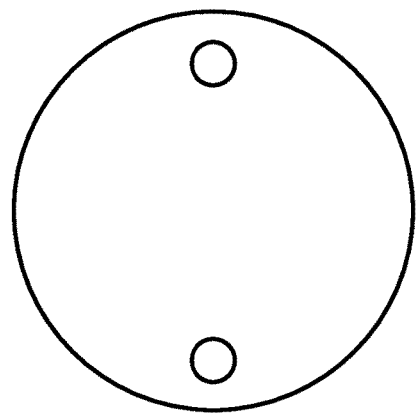
Figure 5:
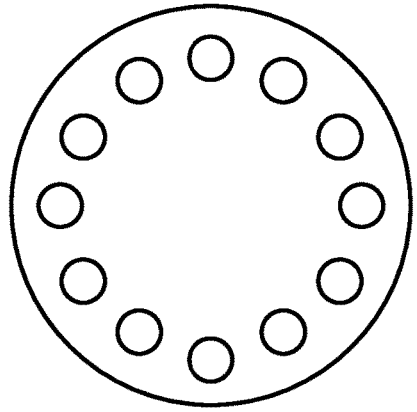
Figure 5:
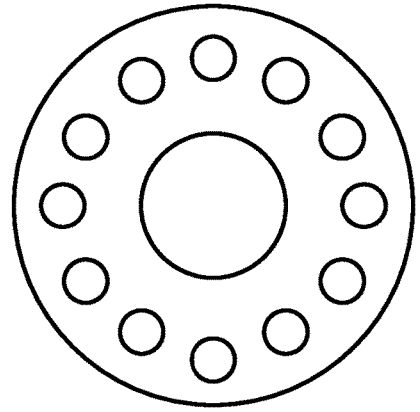

The invention has been described as using a single impedance probe. In alternate embodiments, this impedance probe may be located anywhere radially within the PCP. In yet further alternate embodiments, multiple probes may be used simultaneously, with each probe at substantially the same axial location but radially and/or circumferentially angularly spaced. If there is more than one impedance probe, then the impedance probes may be of different sizes in order to produce different strength magnetic fields and hence induce different eddy currents within the prestressed wires, thereby increasing the variety of measurements and improving the accuracy of anomaly detection. Referring to FIG. 5, various example configurations of impedance probe location within a PCP are shown. In each of the six example configurations shown, the outer circle denotes the PCP and the inner circle or circles denote the impedance probe or probes.

As an alternative to using multiple probes, a single impedance probe having multiple coils can be used. The coils are at substantially the same axial location but radially and/or circumferentially angularly spaced. Unlike an RFT probe, current is driven through each coil and each coil generates a magnetic field. The magnetic field generated by each coil is sufficiently large that it will affect the impedance of the coil and may affect the impedance of other coils in the probe. The impedance of each coil is measured at the plurality of locations, and the measured impedances of all the coils is analyzed for anomalies as described above.

The invention has been described in which the axis of the solenoid coil of the impedance probe is substantially parallel with the axis of the PCP. In an alternate embodiment, the axis of the solenoid coil may have any orientation, such as circumferentially aligned with respect to the PCP or radially aligned with respect to the PCP. In the embodiments in which there are multiple solenoid coils, either as separate impedance probes or as part of the same impedance probe, all coils need not have the same orientation. The coils may also be axially displaced.

The invention has been described using coils of solenoid form. Alternatively, coils of other configurations can be used, such as saddle coils. The embodiments which do not require the axis of the coil to be parallel to the axis of the PCP are particularly apt in this alternative, since the axis of a non-solenoid coil may be difficult to define. However, the coil or coils are still active coils in that they are excited by driving a time-varying current through the coil so as to emit electromagnetic radiation. The impedance of each such coil is measured as part of the PCP inspection.

The invention has been described in which the impedance of the solenoid is recorded as the impedance probe travels along the pipeline. Alternatively, the current in the solenoid can be recorded as the impedance probe travels along the pipeline, and the impedance of the impedance probe at each location determined after the impedance probe has been recovered. The analysis of the impedance for anomalies indicating breaks in the prestressed wire 14 is the same in either case.

The step 52 described above of analyzing the measured impedances is preferably implemented as logical instructions in the form of software. Alternatively, some or all of the logical instructions may be implemented as hardware, or as a combination of software or hardware. If in the form of software, the logical instructions may be stored on non-transitory computer-readable storage media in a form executable by a computer processor, or located within a memory in communication with a computer processor.

The analysis of the measured impedance of the impedance probe can be used for other inspection of the PCP. For example, in addition to or as an alternative to detecting breaks in prestressed wire 14, the measured impedance can be used to verify that pipeline contractors have installed sections of pipe in the correct order. The pressure that can be withstood by a section of pipe is a function partly of the diameter and spacing of the prestressed wire surrounding the concrete of the section of pipe. A weaker section of pipe will therefore induce less current in an impedance probe, and affect the measured impedance differently than would a stronger section of pipe. However, similar weak sections of pipe will produce roughly similar measured impedances as each other, and similar strong sections of pipe will produce roughly similar measured impedances as each other. As the impedance probe travels along a pipeline, the measured impedances can be used to compare different section of pipe. In this way, it can be determined if the sections of pipe have been installed in the correct order.

The embodiments presented are exemplary only and persons skilled in the art would appreciate that variations to the embodiments described above may be made without departing from the spirit of the invention.

I claim:

1. A method of inspecting a prestressed concrete pipe (PCP), comprising:
    passing an impedance probe along the PCP;
    at each of a plurality of locations along the PCP:
        generating a magnetic field by driving a time-varying current through the impedance probe; and
        measuring the impedance of the impedance probe; and
    analyzing the measured impedance at each of the locations.

2. The method of claim 1 further comprising:
    concluding from any unexpected anomaly in the measured impedance that a break in prestressed wire of the PCP is likely at the location associated with the measured impedance containing the unexpected anomaly.

3. The method of claim 1 further comprising:
    determining from the measured impedance a behaviour of the measured impedance for each of a plurality of sections of a pipeline of PCP; and
    determining from the plurality of behaviours a relative strength of the corresponding section.

4. The method of claim 1
    wherein the impedance probe comprises a single coil,
    wherein generating a magnetic field comprises driving the time-varying current through the single coil, and
    wherein measuring the impedance of the impedance probe comprises measuring the impedance of the single coil.

5. The method of claim 4 wherein the single coil is a solenoid.

6. The method of claim 4 wherein the single coil is a saddle coil.

7. The method of claim 1
    wherein the impedance probe comprises a plurality of coils,
    wherein generating a magnetic field comprises driving the time-varying current through each of the coils,
    wherein measuring the impedance of the impedance probe comprises measuring the impedance of each of the coils, and
    wherein analyzing the measured impedance comprises analyzing the measured impedances of all of the coils.

8. The method of claim 7 wherein the coils are at substantially the same axial location relative to the axis of the pipe but radially and/or circumferentially angularly spaced.

9. The method of claim 7 wherein at least one of the coils is a solenoid.

10. The method of claim 7 wherein at least one of the coils is a saddle coil.

11. The method of claim 1 further comprising:
    passing at least one additional impedance probe along the PCP;
    at each of the plurality of locations along the PCP:
        generating a magnetic field by driving a respective time-varying current through each of the at least one additional impedance probe; and
        measuring the impedance of each of the at least one additional impedance probe; and analyzing the measured impedance of each of the at least one additional impedance probe at each of the locations.

12. The method of claim 11 further comprising:

concluding from any unexpected anomaly in any of the measured impedances that a break in prestressed wire of the PCP is likely at the location associated with the measured impedance containing the unexpected anomaly.

* * * * *